(12) United States Patent
Hess et al.

(10) Patent No.: US 11,726,073 B1
(45) Date of Patent: Aug. 15, 2023

(54) COMMERCIAL AND RESIDENTIAL METER BYPASS SYSTEM

(71) Applicant: Honeywell International Inc., Charlotte, NC (US)

(72) Inventors: Keith James Hess, Marlton, NJ (US); Christof Hermann Esselmann, Nordwalde (DE); Ryan Min Chul Kim, North Wales, PA (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 24 days.

(21) Appl. No.: 17/649,739

(22) Filed: Feb. 2, 2022

(51) Int. Cl.
*G01N 33/00* (2006.01)

(52) U.S. Cl.
CPC ....... *G01N 33/007* (2013.01); *G01N 33/0016* (2013.01); *G01N 33/0063* (2013.01)

(58) Field of Classification Search
CPC ............. G01N 33/007; G01N 33/0016; G01N 33/0063
See application file for complete search history.

(56) References Cited

U.S. PATENT DOCUMENTS

| | | | |
|---|---|---|---|
| 3,245,257 A | 4/1966 | Anderson | |
| 3,256,735 A * | 6/1966 | Smith | G01F 15/185 |
| | | | 73/201 |
| 3,266,308 A | 8/1966 | Howarth | |
| 3,272,009 A | 9/1966 | Leopold, Jr. et al. | |
| 5,918,624 A | 7/1999 | Young | |
| 7,347,219 B2 * | 3/2008 | Gohde | F16K 11/20 |
| | | | 73/201 |
| 10,247,594 B2 * | 4/2019 | Smith | G01F 15/185 |
| 2007/0089791 A1 | 4/2007 | Gohde et al. | |
| 2013/0263951 A1 * | 10/2013 | Gardner | F16K 5/0605 |
| | | | 137/625.11 |
| 2020/0149945 A1 | 5/2020 | Yaklin | |
| 2021/0207986 A1 * | 7/2021 | Smith | G01F 15/185 |

FOREIGN PATENT DOCUMENTS

| | | |
|---|---|---|
| EP | 3 396 332 A1 | 10/2018 |
| JP | 3589192 B2 | 10/2002 |
| WO | 2021/133968 A1 | 7/2021 |

OTHER PUBLICATIONS

"Commercial Co-Pilot Meter Bypass System", GF Central Plastics, LLC, Commercial Co-Pilot Announcement | 09-20 Retrieved from: https://www.gfps.com/content/dam/gfps/us/products/meter-connection-products/gfcp-us-announcement-commercial-co-pilot-announcement-en.pdf Retrieved on: Nov. 18, 2021 (2 pages total).

"Residential Co-Pilot Meter Bypass System", GF Central Plastics, LLC, Commercial Co-Pilot Announcement | 09-20 Retrieved from: https://www.gfps.com/content/dam/gfps/us/products/meter-connection-products/gfcp-us-announcement-residential-co-pilot-announcement-en.pdf Retrieved on: Nov. 18, 2021 (2 pages total).

\* cited by examiner

*Primary Examiner* — Francis C Gray
(74) *Attorney, Agent, or Firm* — John Maldjian; Stevens & Lee PC

(57) ABSTRACT

A method includes attaching a gas capture device to a bypass system adjacent to a gas meter. The method also includes rotating an internal cartridge near the gas meter to a bypass mode. The rotation of the internal cartridge enables gas to be diverted through a bypass system and away from the gas meter into an outlet. Remaining gas is captured from the gas meter to prevent the gas from releasing externally. The gas meter is removed from its original position. The internal cartridge is rotated from the bypass mode to a purge mode.

20 Claims, 6 Drawing Sheets

COMMERCIAL AND RESIDENTIAL METER BYPASS SYSTEM

TECHNICAL FIELD

The present disclosure generally relates to a commercial and residential meter bypass system designed to enable gas technicians to service gas meters without gas flow interruption.

BACKGROUND

Commercial and residential meters typically encounter an interruption in gas flow when they need to be replaced. Prior solutions have been given to possibly address this problem.

The prior solutions have attempted to directly release purge gases into the atmosphere. In addition, the prior solutions require cumbersome valve combinations.

Accordingly, with the current solutions, there is not an effective way of containing purge gases. Another problem is that the gas flow is interrupted whenever the gas meter has to be replaced. There is also many cumbersome devices or valve combinations that need to be in place to effectively replace the gas meter.

As such, a need exists to be able to have the gas flow be uninterrupted when the gas meter has to be replaced. The gas flow should be able to continue by some means while another gas meter is replacing the old gas meter.

Further, a need also exists to be able to capture the remaining gas from the old gas meter and any purge gases effectively. Any remaining gas or purge gases should not be released externally into the atmosphere.

SUMMARY

The following summary is provided to facilitate an understanding of some of the features of the disclosed embodiments and is not intended to be a full description. A full appreciation of the various aspects of the embodiments disclosed herein can be gained by taking the specification, claims, drawings, and abstract as a whole.

The aforementioned aspects and other objectives can now be achieved as described herein.

In an embodiment, a method attaching a gas capture device to a bypass system adjacent to a gas meter. The method also includes rotating an internal cartridge near the gas meter to a bypass mode. The rotation of the internal cartridge enables gas to be diverted through a bypass system and away from the gas meter into an outlet, wherein remaining gas is captured from the gas meter to prevent the gas from releasing externally, and wherein the gas meter is removed from its original position. The method also includes rotating the internal cartridge from the bypass mode to a purge mode.

The method also includes replacing the gas meter with another gas meter.

The method also includes rotating the internal cartridge from an open mode to the bypass mode.

The method also includes rotating the internal cartridge from the bypass mode to the purge mode to remove trapped air from the gas meter. In an embodiment, a method includes unlocking and removing any security features within a gas meter bypass. The method also includes attaching an evacuation device to a port and rotating an internal cartridge of the gas meter bypass from an open mode to a bypass mode, wherein placing the internal cartridge in the bypass mode diverts gas through a bypass system away from the gas meter to an outlet, and removing remaining gas from the gas meter. The method also includes removing the gas meter in response to removing the remaining gas from the gas meter.

The bypass mode has a channel system (need to label this "auto pressure relief" channel in FIG. 3 or FIG. 5; bottom arrows in FIG. 3 flow through this channel, but it is not labeled.) that relieves the pressure in the gas meter, wherein tampering is detected when used in conjunction with another connected gas meter in a data network enabled with an automated alarm system to detect when an unexpected drop in pressure occurs in the gas meter.

Tampering is detected when used in conjunction with a connected device enabled with an automated alarm system to detect when a positional sensor is activated by a change in position of the internal cartridge to get to the bypass mode.

The method further includes positioning another gas meter in an initial position by connecting inlet and outlet sides.

In an embodiment, a system includes one or more security features including at least one of a security plate, metal seal wire, tamper tag, or security seal, wherein the one or more security features are removed away from a gas meter bypass. The system also includes an evacuation device that is attached to a port. An internal cartridge of the gas meter is rotated from an open mode to a bypass mode. The internal cartridge is placed in the bypass mode to divert gas through a bypass system away from the gas meter to an outlet, and remaining gas is removed from the gas meter. The system also includes that gas meter being removed from its original position in response to the remaining gas being removed from the gas meter.

The remaining gas is removed or captured to prevent the remaining gas from being released to an external atmosphere.

The internal cartridge is rotated to a purge mode to enable the gas flow through a new gas meter inserted in place of the removed gas meter and purge air from the new gas meter.

The internal cartridge is rotated to an open mode to enable the gas to flow through a new gas meter and away from the bypass system.

BRIEF DESCRIPTION OF THE FIGURES

The accompanying figures, in which like reference numerals refer to identical or functionally similar elements throughout the separate views and which are incorporated and form a part of the specification, further illustrate the present invention and, together with the detailed description of the invention, serve to explain the principles of the present invention.

Figure 1:
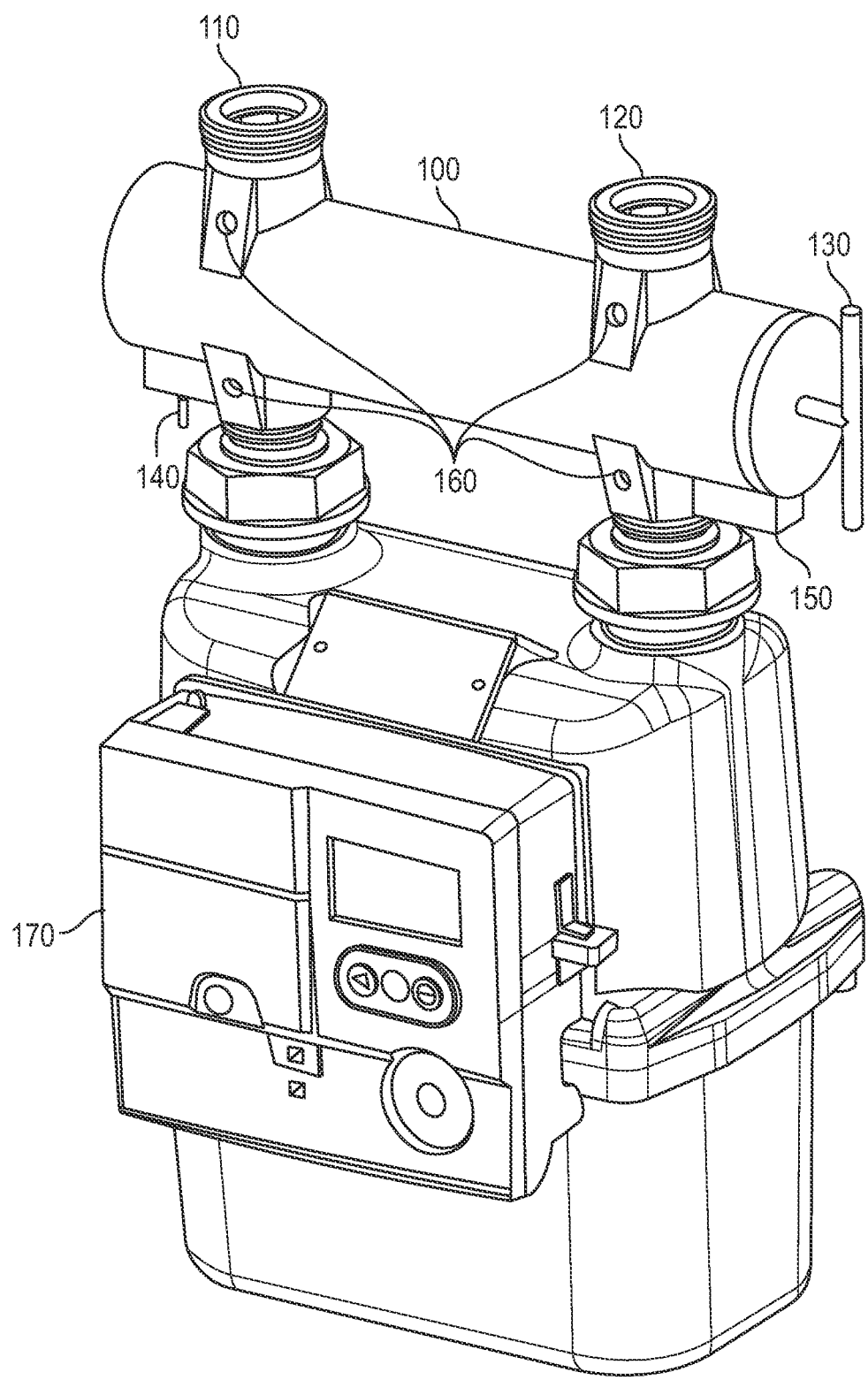
FIG. 1 illustrates a schematic diagram in accordance with an embodiment of the invention.

Unless otherwise indicated illustrations in the figures are not necessarily drawn to scale.

DETAILED DESCRIPTION OF SOME EMBODIMENTS

Background and Context

The particular values and configurations discussed in these non-limiting examples can be varied and are cited merely to illustrate one or more embodiments and are not intended to limit the scope thereof.

Subject matter will now be described more fully herein after with reference to the accompanying drawings, which form a part hereof, and which show, by way of illustration, specific example embodiments. Subject matter may, however, be embodied in a variety of different form and, therefore, covered or claimed subject matter is intended to be construed as not being limited to any example embodiments set forth herein, example embodiments are provided merely to be illustrative. Likewise, a reasonably broad scope for claimed or covered subject matter is intended. Among other issues, subject matter may be embodied as methods, devices, components, or systems. The followed detailed description is, therefore, not intended to be interpreted in a limiting sense.

Throughout the specification and claims, terms may have nuanced meanings suggested or implied in context beyond an explicitly stated meaning. Likewise, phrases such as "in one embodiment" or "in an example embodiment" and variations thereof as utilized herein may not necessarily refer to the same embodiment and the phrase "in another embodiment" or "in another example embodiment" and variations thereof as utilized herein may or may not necessarily refer to a different embodiment. It is intended, for example, that claimed subject matter include combinations of example embodiments in whole or in part.

In general, terminology may be understood, at least in part, from usage in context. For example, terms such as "and," "or," or "and/or" as used herein may include a variety of meanings that may depend, at least in part, upon the context in which such terms are used. Generally, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures, or characteristics in a plural sense. Similarly, terms such as a "a," "an," or "the", again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

One having ordinary skill in the relevant art will readily recognize the subject matter disclosed herein can be practiced without one or more of the specific details or with other methods. In other instances, well-known structures or operations are not shown in detail to avoid obscuring certain aspects. This disclosure is not limited by the illustrated ordering of acts or events, as some acts may occur in different orders and/or concurrently with other acts or events. Furthermore, not all illustrated acts or events are required to implement a methodology in accordance with the embodiments disclosed herein.

Unless defined otherwise, all technical and scientific terms used herein have the same meanings as commonly understood by one of ordinary skill in the art to which the disclosed embodiments belong. Preferred methods, techniques, devices, and materials are described, although any methods, techniques, devices, or materials similar or equivalent to those described herein may be used in the practice or testing of the present invention.

Although claims have been included in this application to specific enumerated combinations of features, it should be understood the scope of the present disclosure also includes any novel feature or any novel combination of features disclosed herein.

References "an embodiment," "example embodiment," "various embodiments," "some embodiments," etc., may indicate that the embodiment(s) so described may include a particular feature, structure, or characteristic, but not every possible embodiment necessarily includes that particular feature, structure, or characteristic.

Headings provided are for convenience and are not to be taken as limiting the present disclosure in any way.

Each term utilized herein is to be given its broadest interpretation given the context in which that term is utilized.

Terminology

The following paragraphs provide context for terms found in the present disclosure (including the claims):

The transitional term "comprising", which is synonymous with "including," "containing," or "characterized by," is inclusive or open-ended and does not exclude additional, unrecited elements or method steps. See, e.g., *Mars Inc.* v. *H.J. Heinz Co.*, 377 F.3d 1369, 1376, 71 USPQ2d 1837, 1843 (Fed. Cir. 2004) ("[L]ike the term 'comprising,' the terms 'containing' and 'mixture' are open-ended."). "Configured to" or "operable for" is used to connote structure by indicating that the mechanisms/units/components include structure that performs the task or tasks during operation. "Configured to" may include adapting a manufacturing process to fabricate components that are adapted to implement or perform one or more tasks.

"Based On." As used herein, this term is used to describe factors that affect a determination without otherwise precluding other or additional factors that may affect that determination. More particularly, such a determination may be solely "based on" those factors or based, at least in part, on those factors.

All terms of example language (e.g., including, without limitation, "such as", "like", "for example", "for instance", "similar to", etc.) are not exclusive of other examples and therefore mean "by way of example, and not limitation . . . "

A description of an embodiment having components in communication with each other does not infer that all enumerated components are needed.

A commercial implementation in accordance with the scope and spirit of the present disclosure may be configured according to the needs of the particular application, whereby any function of the teachings related to any described embodiment of the present invention may be suitably changed by those skilled in the art.

The flowchart and block diagrams in the figures illustrate the architecture, functionality, and operation of possible implementations of systems and methods according to various embodiments. Functions noted in the block may occur out of the order noted in the figures. For example, two blocks shown in succession may, in fact, be executed substantially concurrently, or the blocks may sometimes be executed in the reverse order, depending upon the functionality involved.

Further, any sequence of steps that may be described does not necessarily indicate a condition that the steps be performed in that order. Some steps may be performed simultaneously.

The functionality and/or the features of a particular component may be alternatively embodied by one or more other devices that are not explicitly described as having such functionality/features. Also, various embodiments of the present invention need not include a device itself.

More specifically, as will be appreciated by one skilled in the art, aspects of the present invention may be embodied as a system and/or method. Furthermore, aspects of the present invention may take the form of a plurality of systems to enable gas meter to perform self-checking to determine its overall functioning without requiring a meter operator.

Introduction

Embodiments of the present invention include a means of servicing or replacing a gas meter without interrupting the gas flow. A gas meter is illustrated. A gas capture/evacuation device is attached to a bypass system. An internal cartridge is original at an open position. As the gas meter needs to be serviced or replaced, the internal cartridge outside of the gas meter is rotated from the open mode to a bypass mode. In the bypass mode, the gas flow that was flowing through the gas meter is instead diverted to a bypass system outside of the gas meter. As a result, the gas flow is uninterrupted, and the gas meter can be replaced with another gas meter. A meter evacuation procedure is performed to remove/capture remaining gas from the old gas meter to prevent the remaining gas from being released externally into the atmosphere. The old gas meter is then replaced with a new gas meter with substantially similar configurations. The new gas meter is fully connected by its inlet and outlet sides.

When the new gas meter is positioned in place of the old gas meter, the internal cartridge is rotated from the bypass mode to the purge mode. In the purge mode, gas is diverted through the bypass system and also through the new gas meter to a purge port. The connected gas capture/evacuation device will capture the purge gases and prevent the purge gases from releasing into the external atmosphere. The meter index/odometer of the gas meter will be monitored to ensure a full purge of the internal volume.

Once the purge has been completed, the internal cartridge will be rotated from the purge mode to the open mode. In the open mode, the gas flow will not be diverted to the bypass system. Instead, the gas flow will flow through the gas meter.

Embodiments of the present invention will show how the gas meter is replaced with another gas meter, and illustrate the processes involved in the bypass mode and purge mode.

System Structure

FIG. 1 illustrates a gas meter 170 connected to a gas meter bypass 100 within a system that include ports 110, 120. A gas meter bypass 100 can include anywhere of up to four primary ports along with ten auxiliary ports in a given configuration. Ports 110, 120, 140, 150, and 160 are illustrated in this embodiment. The ports 110, 120 can be utilized as inlet and outlet ports, while ports 140, 150, and 160 can be sensor ports, purge ports, and evacuation/capture ports for the gas flow that is flowing within the gas meter bypass 100. An internal cartridge 130 is also shown. The internal cartridge 130 can be in an open mode, bypass mode, and purge mode. When the internal cartridge 134) is in the open mode, the gas flow will flow through the gas meter 170. When the internal cartridge 130 is rotated to a bypass mode from the open mode, the gas flow is diverted through a bypass system, and will no longer be flowing through the gas meter 170. When the gas meter 170 needs to be serviced and/or replaced, the internal cartridge 130 can be rotated to the bypass mode to enable the gas flow to be diverted to the bypass system, and thereby enable the gas meter 170 to be replaced or serviced. The internal cartridge 130 can also be rotated to a purge mode. In the purge mode, the gas flow will be through the bypass system and also flowing through the gas meter 170 to the purge port 150. The purge gases will then be captured by the connected gas capture/evacuation device.

In FIG. 1, when the gas meter 170 is ready to be serviced or replaced, any locks or security features to the gas meter bypass can be removed. The security features can include, but are not limited to, security plates, meter seal wires, tamper tags, and security seals. The gas meter bypass 100 system can have several tamper indicators that include a detectable automatic pressure relief feature when placed in bypass mode, or with security seals and visual indicators. The bypass system can be used in conjunction with a smart gas meter such as a AC-250NXS as an example.

Figure 2:
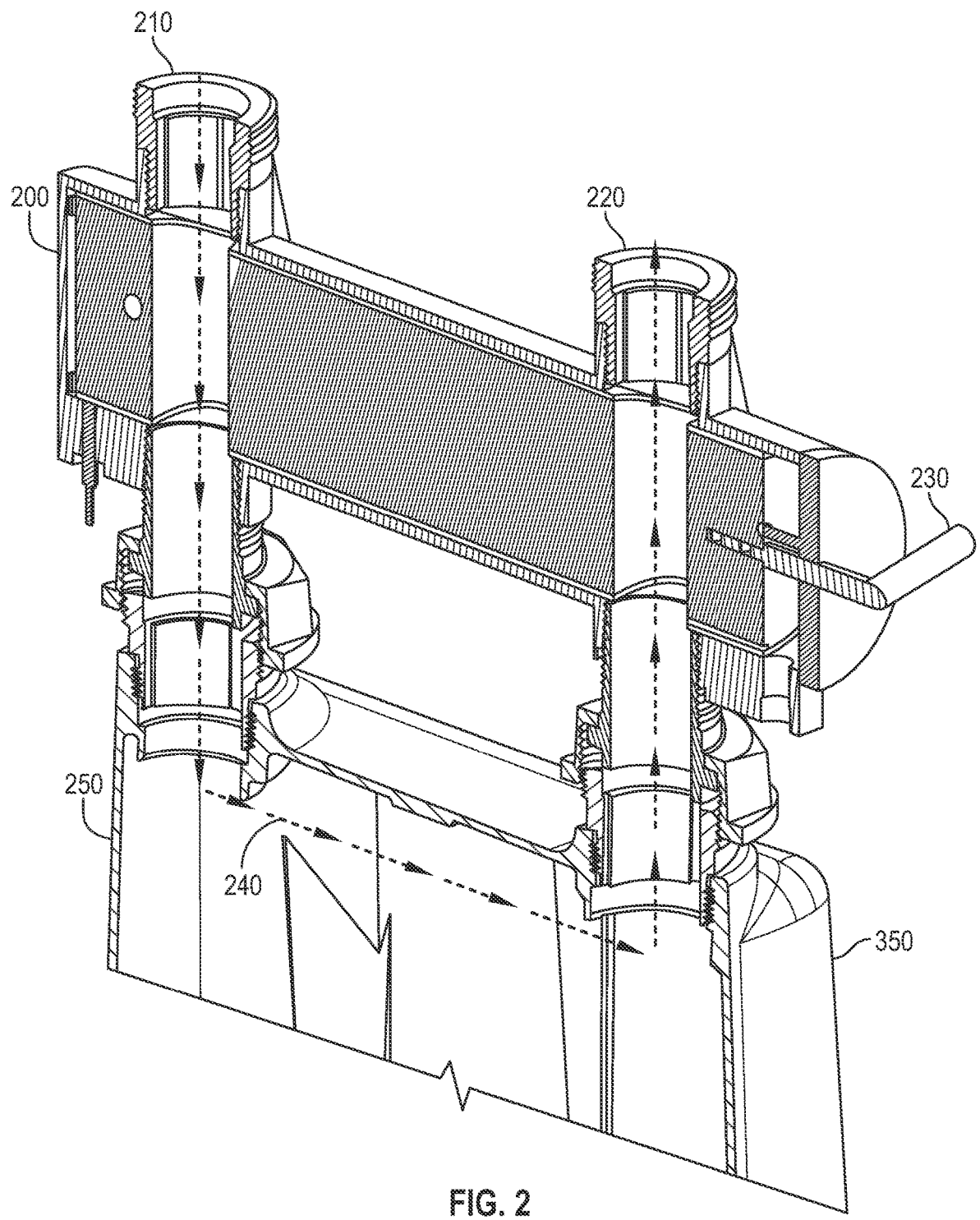
FIG. 2 illustrates another aspect of the schematic diagram in accordance with an embodiment of the invention.

FIG. 2 illustrates a cross-section view of a gas meter 250 and gas meter bypass 200. A further illustration of the gas flow within the gas meter bypass 200 and gas meter 250 is shown. The gas meter bypass 200 will include ports 210, and 220, and an internal cartridge 230. The gas flow 240 flowing within the gas bypass meter 200 is shown. The internal cartridge 230 is in the open mode. When the internal cartridge is in the open mode, the gas flow 240 will consistently flow through the gas bypass meter 200. At a later time interval, the gas meter 250 will have the need to either be serviced or replaced. The gas flow 240 that occurs cannot be interrupted due to the service of the gas meter. As such, despite the service or replacement of the gas meter 250, the gas flow 240 can be continued. There will be another means in which the gas flow will continue to flow while the gas meter 250 is replaced or serviced, wherein the internal cartridge 230 will be rotated to the bypass mode. Moreover, the gas flow 240 will be diverted to a gas meter bypass 200 system.

Figure 3:
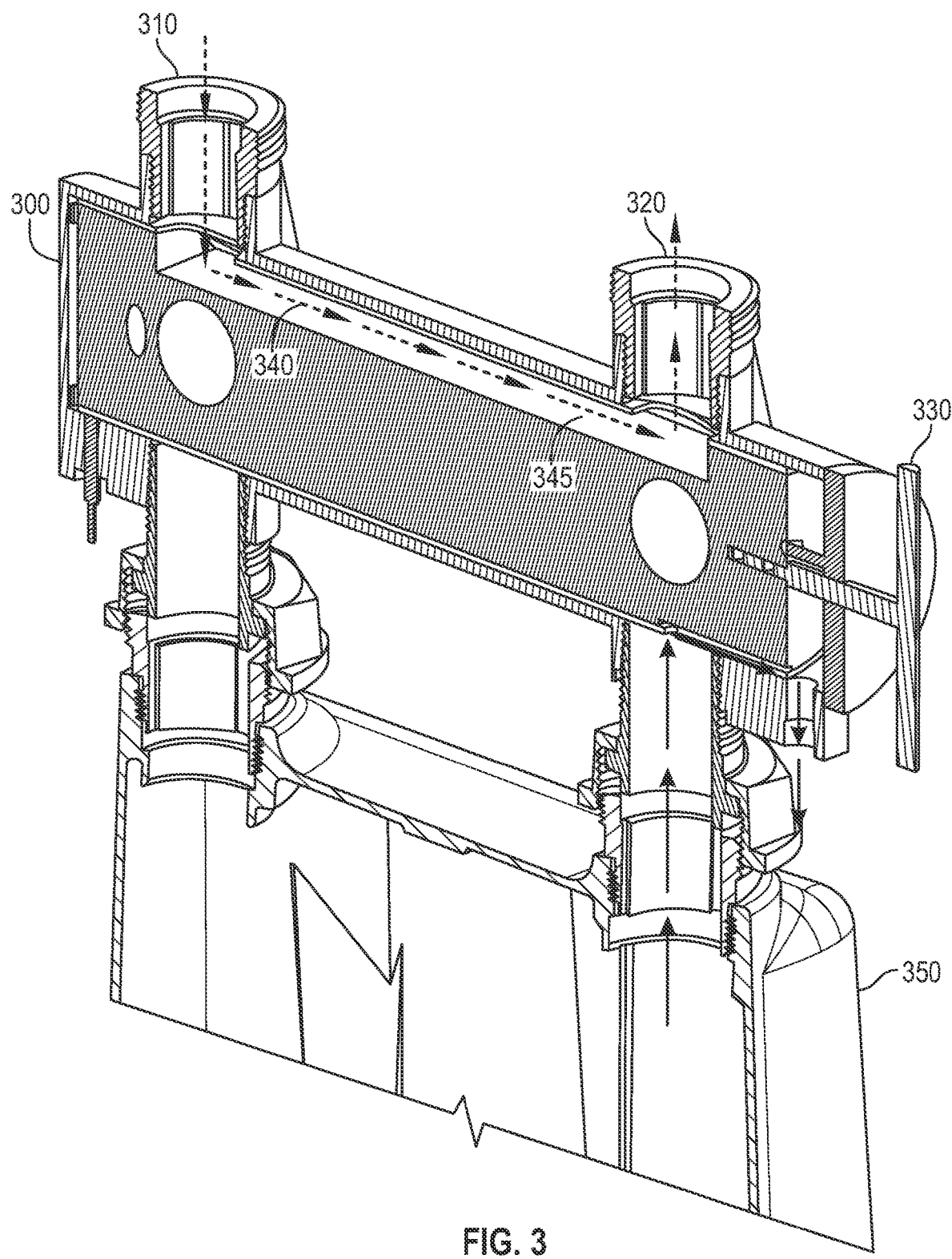
FIG. 3 illustrates a further aspect of the schematic diagram in accordance with an embodiment of the invention.

Referring to FIG. 3, the bypass mode is illustrated in further detail. An embodiment is illustrated in which gas flow is redirected from the gas meter through a bypass system due to the gas meter having to be serviced or replaced. As a result, the gas flow is not interrupted despite the repair or replacement of the gas meter.

In FIG. 3, a gas meter bypass 300 is shown that is substantially similar to the gas meter bypass 100, 200 of FIGS. 1 and 2. In addition, ports 310, 320, and an internal cartridge 330 are also illustrated along with the gas meter 350. In addition, gas flow 340 and a bypass system 345 are also shown, wherein the bypass system 345 will be area in which the gas flow 340 will be diverted in place of the gas meter 350. As the gas meter 350 has to be serviced or replaced, the internal cartridge 330 is rotated to a bypass mode to enable the gas flow 340 to continue without interruption. When the internal cartridge 330 is in the bypass mode, the gas flow 340 is not interrupted. The gas flow 340 has been diverted from the gas meter 300 to the bypass system 345. In addition, the internal cartridge 330 has been rotated from the open mode (shown in FIG. 2), to the bypass mode. As mentioned above, when the internal cartridge 330 is rotated to the bypass mode, the gas flow 340 is diverted from the gas meter 300 to the bypass system 345. The gas flow 340 will continue to flow uninterrupted through the bypass system 345, and not through the gas meter 300 as the gas meter 300 is being replaced. Moreover, the continuous and uninterrupted flow of the gas flow 340 through the bypass system 345 will enable the gas meter 350 to be replaced by another gas meter.

With respect to FIG. 3, a meter evacuation procedure is performed to replace the gas meter 350. Further, the meter evacuation procedure is essentially performed when the gas meter 350 has to be replaced. The meter evacuation procedure will involve removing remaining gas from within the gas meter 350 and preventing a release of the remaining gas to the external atmosphere. In addition, the meter evacuation procedure will also involve capturing the remaining gas from within the gas meter 350 and preventing the captured remaining gas from releasing into the external atmosphere. The meter evacuation procedure also involves removing the gas meter 350 and replacing the gas meter 350 with another gas meter with substantially similar configurations as the gas meter 350. The new gas meter is placed in the original position of the old gas meter 350 by fully connecting inlet and outlet sides for the new gas meter.

Figure 4:
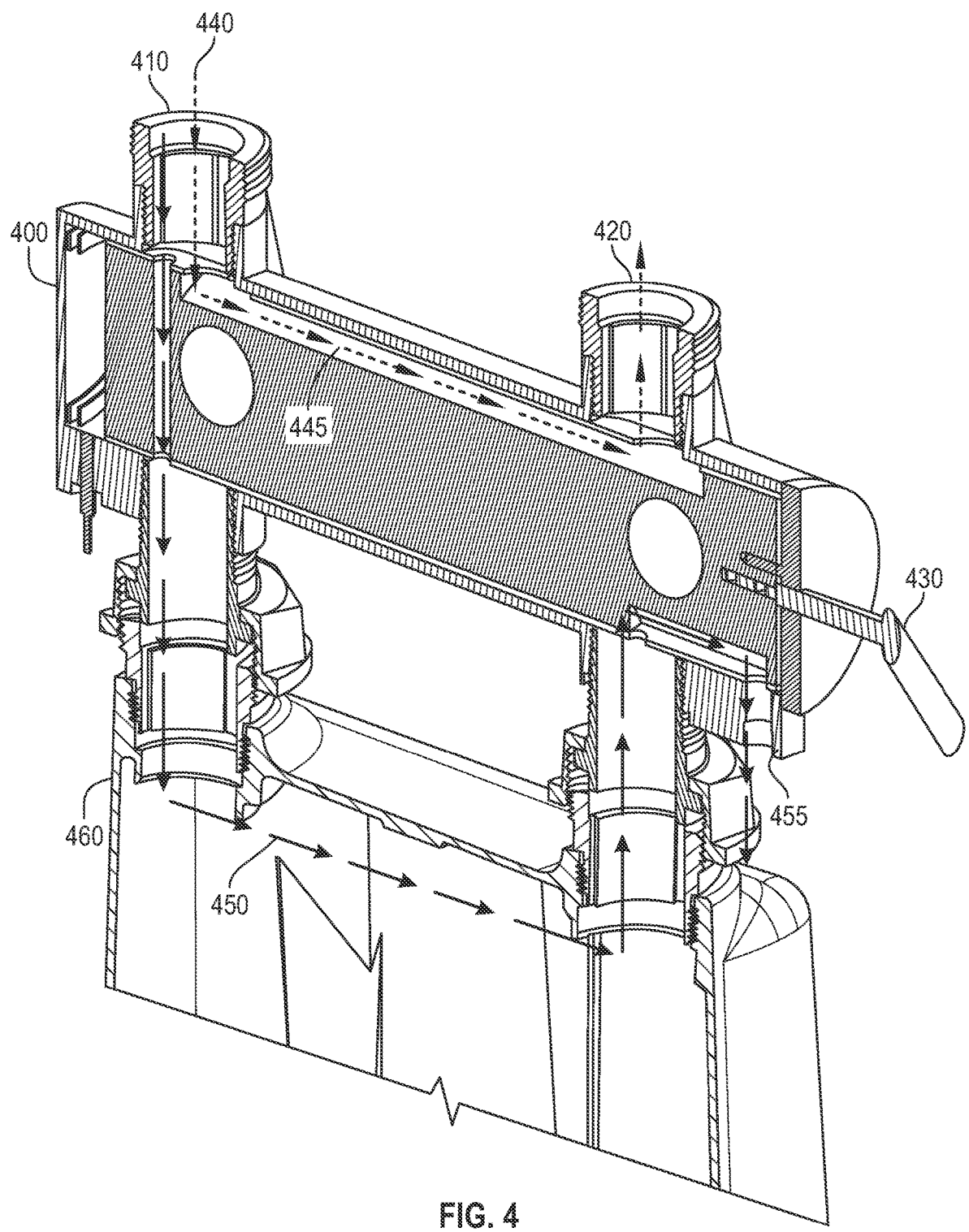
FIG. 4 illustrates another aspect of the schematic diagram in accordance with an embodiment of the invention.

FIG. 4 illustrates the purge mode. Moreover, an embodiment in which the internal cartridge is rotated from the bypass mode to the purge mode is shown. A new gas meter 460 has been placed in place of the old gas meter. The new gas meter bypass 400 system can be substantially similar in configuration to the gas meter bypass shown in FIGS. 1-3. Ports 410, 420 are illustrated. An internal cartridge 430 is illustrated. The ports 410, 420 and internal cartridge 430 are substantially similar to what was illustrated in FIGS. 1-3. A bypass system 445 is also illustrated. In addition, the bypass system gas flow 440 and gas flow 450 through the new gas meter 460 and purge port 455 are also shown.

Referring to FIG. 4, to begin the purge process, the internal cartridge 430 is rotated from the bypass mode to the purge mode. Once the internal cartridge 430 is in the purge mode, the gas flow 440, 450 is diverted through the bypass system 445 and also through the gas meter 460 to a purge port 455. The internal cartridge 430 remains in the purge mode during this process to enable purge gases to be captured. One or more connected gas capture/evacuation devices can capture the purge gases. In addition, the gas meter index/odometer can be monitored to ensure that a full purge of the internal volume of the purge gases has occurred, Once a full purge has occurred, due to the purge gases being captured, the internal cartridge 430 will be rotated from the purge mode to the open mode, When the internal cartridge is in the open mode, the flow of gas will be flowing through the gas meter 460 and will no longer be diverted through the bypass system 445 of the gas meter bypass 400. In addition, any of the one or more evacuation and purge devices can be removed, and any other security features can be replaced. The gas meter 460 can then be locked securely.

Figure 5:
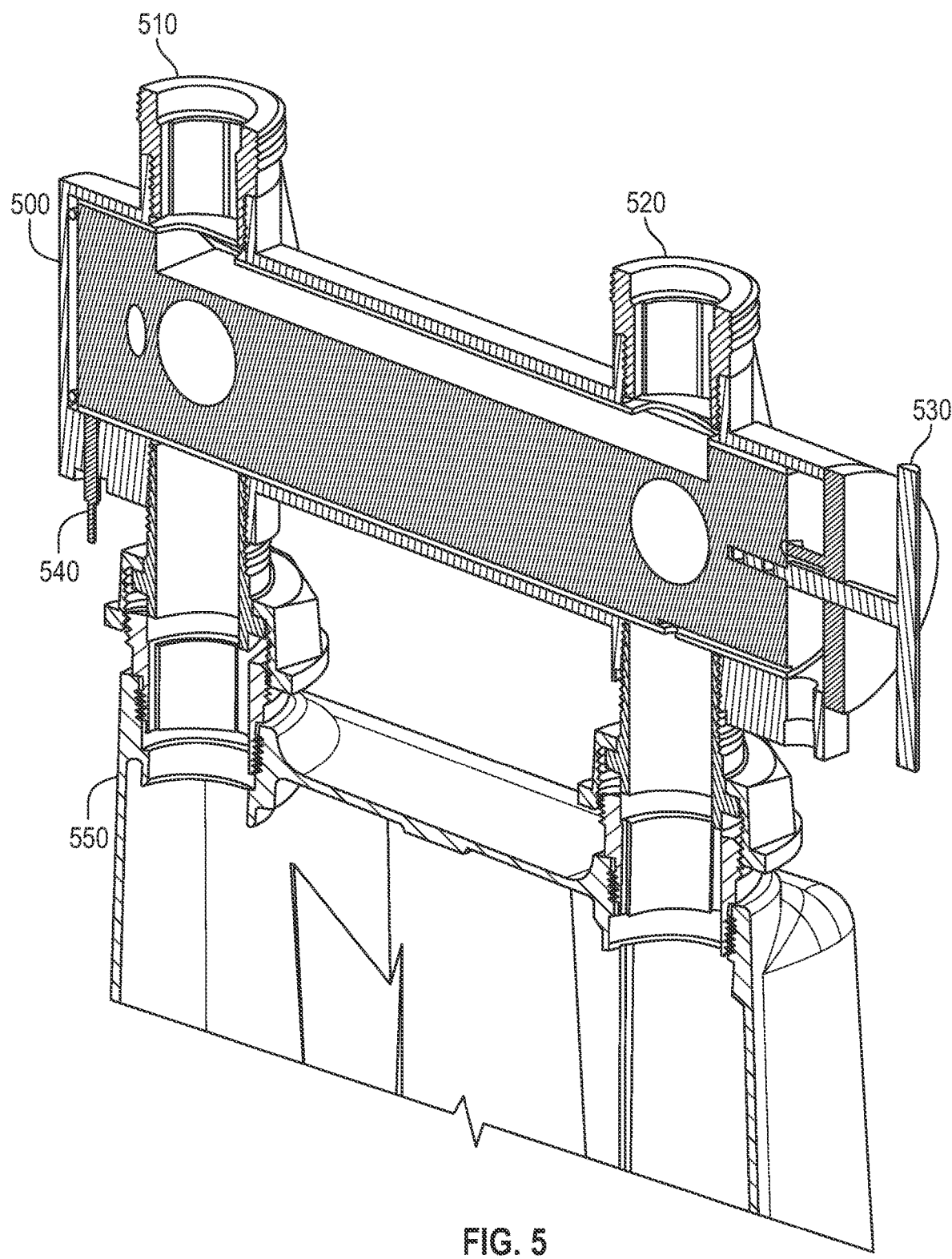
FIG. 5 illustrates a further aspect of the schematic diagram in accordance with an embodiment of the invention.

In FIG. 5, the security feature of a gas meter bypass 500 is shown and a gas meter 550. The gas meter bypass 500 and gas meter 550 are substantially similar to the gas meter bypass shown in FIGS. 1-4, Ports 510, 520 are shown, An internal cartridge 530 is also illustrated. Further, a tamper proximity switch 540 is also illustrated. The tamper proximity switch 540 can be used in conjunction with another connected gas meter or device within the same system as the gas meter bypass 500 to provide tamper detection for the gas meter 550.

With respect to FIG. 5, tamper detection can be part of the gas meter's 550 safety features. With tamper detection, it can be detected when there is an unexpected drop in pressure of the gas meter 550 via an auto pressure relief channel. In addition, it can be detected when a positional sensor such as the tamper proximity switch 540 is activated by a change in position of the internal cartridge 530 to the bypass mode.

Referring to FIGS. 5., tampering can be detected when the gas meter bypass 500 is used in conjunction with another gas meter in same the data network as the gas meter bypass 500. The other gas meter will be configured with an automated alarm system. The pressure sensor (not shown) and automated alarm system within the other connected gas meter 550 will detect when an unexpected pressure drop occurs. Further, tampering will also be detected when the gas meter bypass 500 is used in conjunction with a connected device within the network that is enabled with an automated alarm system. With this configuration, tampering can be detected when a positional sensor such as the proximity switch 540 is activated by a change in position of the internal cartridge 530 to get to the bypass mode.

In FIG. 5, overall, tampering can be detected by the gas meter bypass in conjunction with another connected device or gas meter configured with an automated alarm system that along with the proximity switch 540, is able to determine an unexpected drop in pressure and the position of the internal cartridge.

Figure 6:
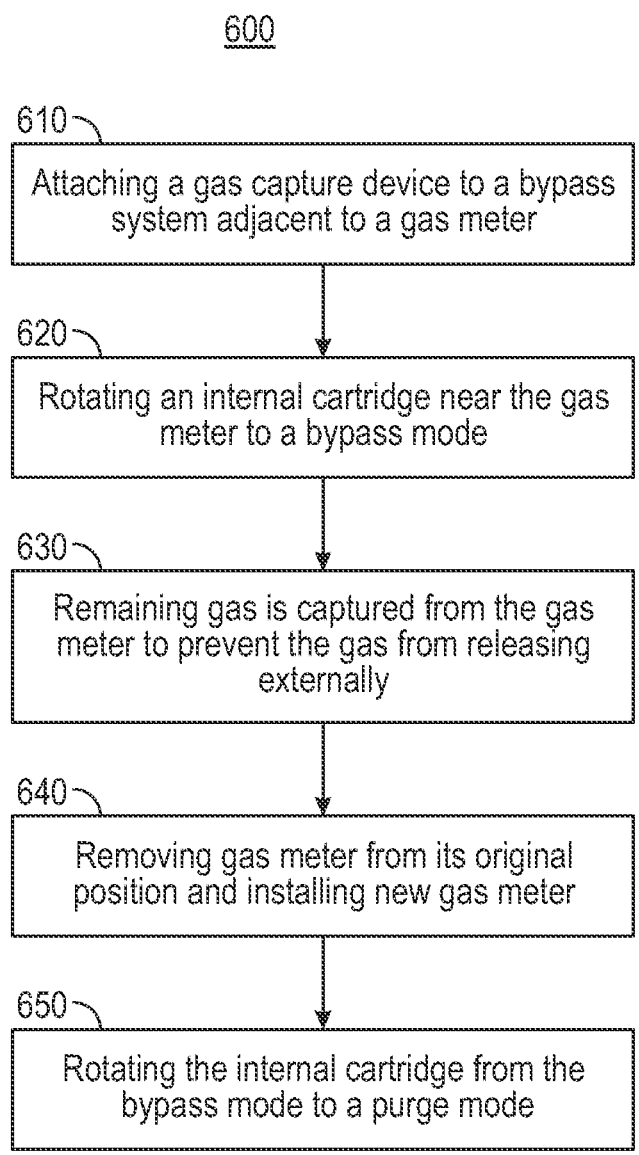
FIG. 6 illustrates a flow chart in accordance with an embodiment of the invention.

Referring to FIG. 6, a process 600 is illustrated in which a gas meter that needs to be replaced is replaced by another gas meter using a bypass procedure. With the meter bypass procedure, the gas flow is not interrupted in spite of the gas meter being replaced by another gas meter.

In FIG. 6, at step 610, a gas capture device is attached to a bypass system adjacent to the gas meter. The gas capture device can be used to capture gases that are purged from the gas meter to prevent these purged gases from escaping into the external atmosphere. The gas capture device can also capture remaining gas from the gas meter that is to be replaced as well.

Referring to FIG. 6, at step 620, the internal cartridge outside of the gas meter is rotated. Initially, when gas is flowing through the gas meter, the internal cartridge is an open mode. However, when the gas meter needs to be replaced, the internal cartridge is rotated to a bypass mode. In the bypass mode, the gas is diverted from the gas meter to a bypass system outside of the gas meter. As such, the gas flow is not interrupted although the gas meter is being replaced.

In FIG. 6, at step 630, the remaining gas is captured from the gas meter to prevent the remaining gas from releasing externally. During the bypass mode, when the internal cartridge is rotated to the bypass mode, the gas capture device will capture the remaining gas to prevent the remaining gas from being released to the external atmosphere.

With respect to FIG. 6, at step 640, the gas meter is replaced with another gas meter. The new gas meter is placed in the original position of the previous gas meter. As the old gas meter had to be replaced, the gas flow was thereby still continued through the bypass system. The new gas meter is fully positioned by fully connecting the inlet and outlet sides of the new gas meter. As such, the non-interruption of the gas flow enabled the old gas meter to be replaced by the new gas meter.

In FIG. 6, at step 650, the internal cartridge is rotated from the bypass mode to a purge mode. During the purge mode, the gas is diverted through the bypass system and also through the gas meter to a purge port. The purged gases from the gas meter and bypass system will be captured by the gas capture evacuation device. In addition, in the purge mode, the gas meter index/odometer is monitored to ensure a full purge of the internal volume of the gas. Once the gas has been purged, the internal cartridge is rotated from the purge mode to the open mode. In the open mode, the gas is flowing through the gas meter and no longer being diverted to the bypass system. The evacuation/purge device is then removed, and any security features are then replaced.

Those skilled in the art will appreciate that the example embodiments are non-exhaustive and that embodiments other than that described here may be included without departing from the scope and spirit of the presently disclosed embodiments.

Advantages/Summary

Overall, an effective means of replacing the gas meter in need of service or replacement is illustrated without interrupting the gas flow that or causing unwanted gas to be related to the open external atmosphere outside of the gas meter. A new gas meter can replace the old gas meter without causing any interruption to the gas flow, and without releasing any unwanted gas into the external atmosphere.

In the open mode, in the gas flow is flowing through the gas meter. When the gas meter needs to be replaced, the internal cartridge is moved from the open mode to a bypass mode. In the bypass mode, the gas flow is diverted from the gas meter to the bypass system. As the gas flow is diverted to the bypass system and no longer flowing through the gas meter that needs to be replaced. A meter evacuation procedure is performed to remove/capture remaining gas from the gas meter and preventing the remaining gas from releasing into the atmosphere. The gas meter is removed then and replaced with the new gas meter. The new gas meter is thereby fully connected by both its inlet and outlet sides.

After the new gas meter has been installed, the internal cartridge is rotated from the bypass mode to the purge mode. In the purge mode, gas is diverted through the bypass system and is also flowing through the gas meter to the purge port, A connected gas capture/evacuation device will then capture the purge gases. The gas meter index/odometer is monitored to ensure a full purge of the internal volume of the purge gases.

Once the purge gases have been captured, the internal cartridge can be rotated from the purge mode to the open mode. In the open mode, the gas flow is no longer diverted to the bypass system. The gas flow will be flowing through the new gas meter. The evacuation/purge device will be removed. The lock around the gas meter will be locked, and any security features will be thereby removed.

Conclusion

All references, including granted patents and patent application publications, referred herein are incorporated herein by reference in their entirety.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Various aspects of the invention have been described above by way of illustration, and the specific embodiments disclosed are not intended to limit the invention to the particular forms disclosed. The particular implementation of the system provided thereof may vary depending upon the particular context or application. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

The corresponding structures, materials, acts, and equivalents of all means or step plus function elements in the claims below are intended to include any structure, material, or act for performing the function in combination with other claimed elements as specifically claimed.

What is claimed is:

1. A method comprising:
    attaching an evacuation device to a port and rotating an internal cartridge of a gas meter bypass from an open mode to a bypass mode and removing gas from the gas meter, wherein the rotation of the internal cartridge enables gas to be diverted through a bypass system and away from the gas meter into an outlet, wherein remaining gas is captured from the gas meter to prevent the gas from releasing externally, and wherein the gas meter is removed from its original position; and
    rotating the internal cartridge from the bypass mode to a purge mode.

2. The method of claim 1, further comprising:
    replacing the gas meter with another gas meter.

3. The method of claim 1, further comprising:
    rotating the internal cartridge from an open mode to the bypass mode.

4. The method of claim 1, wherein the internal cartridge is rotated from the bypass mode to the purge mode to remove trapped gas from the gas meter.

5. The method of claim 1, wherein the gas is diverted through the bypass system when the internal cartridge is placed in the bypass mode.

6. The method of claim 1, further comprising:
    rotating the internal cartridge from the purge mode to the open mode.

7. The method of claim 1, further comprising:
    removing the evacuation device.

8. A method comprising:
    unlocking and removing any security features within a gas meter bypass;
    attaching an evacuation device to a port and rotating an internal cartridge of the gas meter bypass from an open mode to a bypass mode, wherein placing the internal cartridge in the bypass mode diverts gas through a bypass system away from the gas meter to an outlet, and removing remaining gas from the gas meter; and
    removing the gas meter in response to removing the remaining gas from the gas meter.

9. The method of claim 8, wherein the bypass mode has a channel system that relieves the pressure in the gas meter, wherein tampering is detected when used in conjunction with another connected gas meter in a data network, enabled with an automated alarm system to detect when an unexpected pressure drop occurs in the gas meter.

10. The method of claim 8, wherein tampering is detected when used in conjunction with a connected device enabled with an automated alarm system to detect when a positional sensor is activated by a change in position of the internal cartridge to get to the bypass mode.

11. The method of claim 8, further comprising:
positioning another gas meter in an initial position by connecting inlet and outlet sides.

12. The method of claim 8, further comprising:
a gas capture device configured to capture purge gases.

13. The method of claim 8, wherein the internal cartridge is rotated from the bypass mode to a purge mode in response to another gas meter being positioned in place of the first gas meter.

14. The method of claim 8, further comprising:
rotating the internal cartridge from a purge mode to an open mode in response to a full purge of an internal gas volume within the gas meter.

15. A system comprising:
one or more security features including at least one of a security plate, metal seal wire, tamper tag, or security seal, wherein the one or more security features are removed away from a gas meter bypass;
an evacuation device that is attached to a port, wherein an internal cartridge of the gas meter is rotated from an open mode to a bypass mode, wherein placing the internal cartridge in the bypass mode diverts gas through a bypass system away from the gas meter to an outlet, and remaining gas is removed from the gas meter; and
the gas meter removed from its original position in response to the remaining gas being removed from the gas meter.

16. The system of claim 15, wherein the remaining gas is removed or captured to prevent the remaining gas from being released to an external atmosphere.

17. The system of claim 15, further comprising:
another gas meter configured to replace the removed gas meter.

18. The system of claim 15, wherein the internal cartridge is rotated to a purge mode to enable the gas to flow through a new gas meter inserted in place of the removed gas meter and purge air from the new gas meter.

19. The system of claim 15, wherein the internal cartridge is rotated to an open mode to enable the gas to flow through a new gas meter and away from the bypass system.

20. The system of claim 15, wherein the internal cartridge is rotated to the bypass mode to enable the gas to keep flowing through the bypass system and allow the gas meter to be replaced.

* * * * *